United States Patent [19]
Barnum et al.

[11] Patent Number: 5,778,895
[45] Date of Patent: Jul. 14, 1998

[54] METHOD OF DISCRIMINATING BACTERIAL FROM ASEPTIC MENINGITIS

[75] Inventors: Scott R. Barnum. Sterrett; Phillip Stahel. Birmingham. both of Ala.

[73] Assignee: UAB Research Foundation. Birmingham, Ala.

[21] Appl. No.: 790,611

[22] Filed: Jan. 29, 1997

[51] Int. Cl.$^6$ .................................................. A61B 19/00
[52] U.S. Cl. ........................... 128/898; 436/821; 436/811
[58] Field of Search ........................... 128/898; 514/898; 604/51, 49; 436/821, 811

[56] References Cited

U.S. PATENT DOCUMENTS 4,642,284  2/1987  Cooper et al. ............................ 435/7

OTHER PUBLICATIONS

Teisner et al. "Factor I deficeincy and C3 nephritic factor" Scand J Immunol. 20:291–7, Dec. 1984.

Beatty et al. "Complement abnormalities during an epidemic of group B meningococcal infection in children" Clin exp Immunol 64:465–70, 1986.

Fernandez–Sola et al. "Persistent low C3 levels asociated with meningococcal meningitis and mebranoproliferative glomerulonephritis" Am J Nephrol 10:426–30, 1990.

Barnum et al. "Production and interferon–gamma–mediated regulation of complement compound C2 and factors B and D by the astroglioma cell line U105–MG" 287:595–601, 1992.

Bonnin et al. "Complement factor I deficeincy with recurrent aseptic meningitis" Arch intern med 153:1380–3, Jun. 1993.

Kossmann et al. "Elevated levels of the complement components C3 and factor B in ventricular cerebrospinal fluid of patients with traumatic brain injury" J. Neuroimmunol 73:63–9, 1997.

*Primary Examiner*—V. Millin
*Assistant Examiner*—Kelly O'Hara
*Attorney, Agent, or Firm*—Benjamin Aaron Adler, J.D.

[57] ABSTRACT

The present invention provides a method for the differential diagnosis of bacterial meningitis in an individual in need of such diagnosis, comprising the steps of: measuring the levels of complement C3 and complement factor B in the cerebrospinal fluid of the individual; and determining whether that individual has bacterial menigitis based on the levels of complement C3 and complement factor B in the cerebrospinal fluid of that individual. Also provided is a method for the differential diagnosis of bacterial menigitis in an individual in need of such diagnosis, comprising the steps of: measuring the levels of complement factor B in a sample from the individual; and determining whether that individual has bacterial menigitis based on the levels of complement factor B in the sample from that individual.

14 Claims, 1 Drawing Sheet

METHOD OF DISCRIMINATING BACTERIAL FROM ASEPTIC MENINGITIS

FEDERAL FUNDING LEGEND

This research was supported in part by the U.S. government by NIH grant NS29719. Consequently, the government has certain rights in this invention.

BACKGROUND OF THE INVENTION

1. Field of the Invention

The present invention relates generally to the fields of medicine, neuroimmunology and protein chemistry. More specifically, the present invention relates to a method of discriminating bacterial from aseptic meningitis.

2. Description of the Related Art

Bacterial meningitis occurs in about 25,000 cases per year in the United States with an overall mortality rate of from 10–35%. About 30% of individuals with acute bacterial meningitis experience seizures and about 10–30% of those who survive a case of bacterial meningitis exhibit long-term neurological sequelae.

Bacterial meningitis remains a major cause of morbidity and mortality, with a high incidence of residual neurological impairment (reviewed in Quagliarello & Scheld 1992). Early diagnosis and immediate onset of adequate antimicrobial treatment are essential for the survival of patients with bacterial meningitis (Lieu et al. 1992). However, establishing the diagnosis of bacterial meningitis represents a difficult task in most cases, since clinical signs of acute meningitis are non-specific, and laboratory examinations of cerebrospinal fluid (CSF) often do not accurately differentiate between bacterial and aseptic meningitis (Lindquist et al. 1988, Rodewald et al. 1991). Accurate differentiation between bacterial and aseptic (viral) meningitis is difficult as both are inflammatory diseases that elicit similar host defense responses and clinical symptoms. Differential diagnosis can be made on positive identification of the bacteria from the cerebrospinal fluid of the affected individual. Unfortunately, it may take several days to grow and identify the bacteria and twenty-five percent of the time culture results are negative or equivocal even though the patients have bacterial meningitis. Similar or greater error rates affect nearly every laboratory parameter used for diagnostic purposes.

Due to the beneficial effects of early therapy in bacterial meningitis, antibiotics are often started before etiologic diagnosis is established (Lieu et al. 1992). As a consequence, a high rate of patients with aseptic meningitis receive unnecessary antibiotic treatment, leading to prolonged hospitalization and an increased financial burden to the health care system (Rodewald et al. 1991, Lieu et al. 1992).

Only few laboratory parameters in the cerebrospinal fluid determine bacterial meningitis with almost absolute certainty, such as positive cerebrospinal fluid culture and Gram staining (Rodewald et al. 1991, Hoen et al. 1995). Although highly specific, these parameters show very low sensitivities (Rodewald et al. 1991, Hoen et al. 1995), and are therefore not useful in ruling out bacterial infection. In addition to microbiological analysis, non-specific parameters in the cerebrospinal fluid are commonly used for the differential diagnosis of bacterial versus aseptic meningitis, such as total and differential cerebrospinal fluid leukocyte count, cerebrospinal fluid protein and glucose concentrations, CSF/serum glucose ratio, cerebrospinal fluid lactate and C-reactive protein levels (reviewed in Lindquist et al. 1988). However, the diagnostic value of these parameters remains controversial, since their range of distribution overlaps widely in aseptic and bacterial cerebrospinal fluid (Lindquist et al. 1988, Spanos et al. 1989, Rodewald et al. 1991, Hoen et al. 1995).

Two different predictive models have established a mathematical discriminant for the probability of bacterial versus aseptic meningitis, using a combination of clinical, laboratory and epidemiological data (Spanos et al. 1989, Hoen et al. 1995). These models, although accurate, are cumbersome and rarely used in a clinical setting. The identification of a single parameter that could serve as a reliable discriminant in the differential diagnosis of acute meningitis would be of high clinical value.

The prior art is deficient in the lack of accurate and cost effective means of discriminating bacterial from aseptic meningitis. The present invention fulfills this longstanding need and desire in the art.

SUMMARY OF THE INVENTION

Bacterial meningitis is characterized by high mortality and a high rate of persistent neurological impairment. Rapid etiologic diagnosis is essential for the adequate clinical management of patients with bacterial meningitis. Unfortunately, non-specific clinical symptoms and early laboratory findings often do not unequivocally differentiate between bacterial and aseptic meningitis. Therefore, the identification of a single discriminating parameter would be of high value in the differential diagnosis of acute meningitis.

In one embodiment of the present invention, there is provided a method for the differential diagnosis of bacterial meningitis in an individual in need of such diagnosis, comprising the steps of: measuring the levels of complement C3 and complement factor B in the cerebrospinal fluid of said individual; and determining whether said individual has bacterial meningitis based on the levels of complement C3 and complement factor B in the cerebrospinal fluid of said individual.

In another embodiment of the present invention, there is provided a method for the differential diagnosis of bacterial meningitis in an individual in need of such diagnosis, comprising the steps of: measuring the levels of complement factor B in a sample from said individual; and determining whether said individual has bacterial meningitis based on the levels of complement factor B in the sample from said individual.

In another embodiment of the present invention, there is provided a method for the differential diagnosis of bacterial meningitis in an individual in need of such diagnosis, comprising the steps of: measuring the levels of complement C3 in a sample from said individual; and determining whether said individual has bacterial meningitis based on the levels of complement C3 in the sample from said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
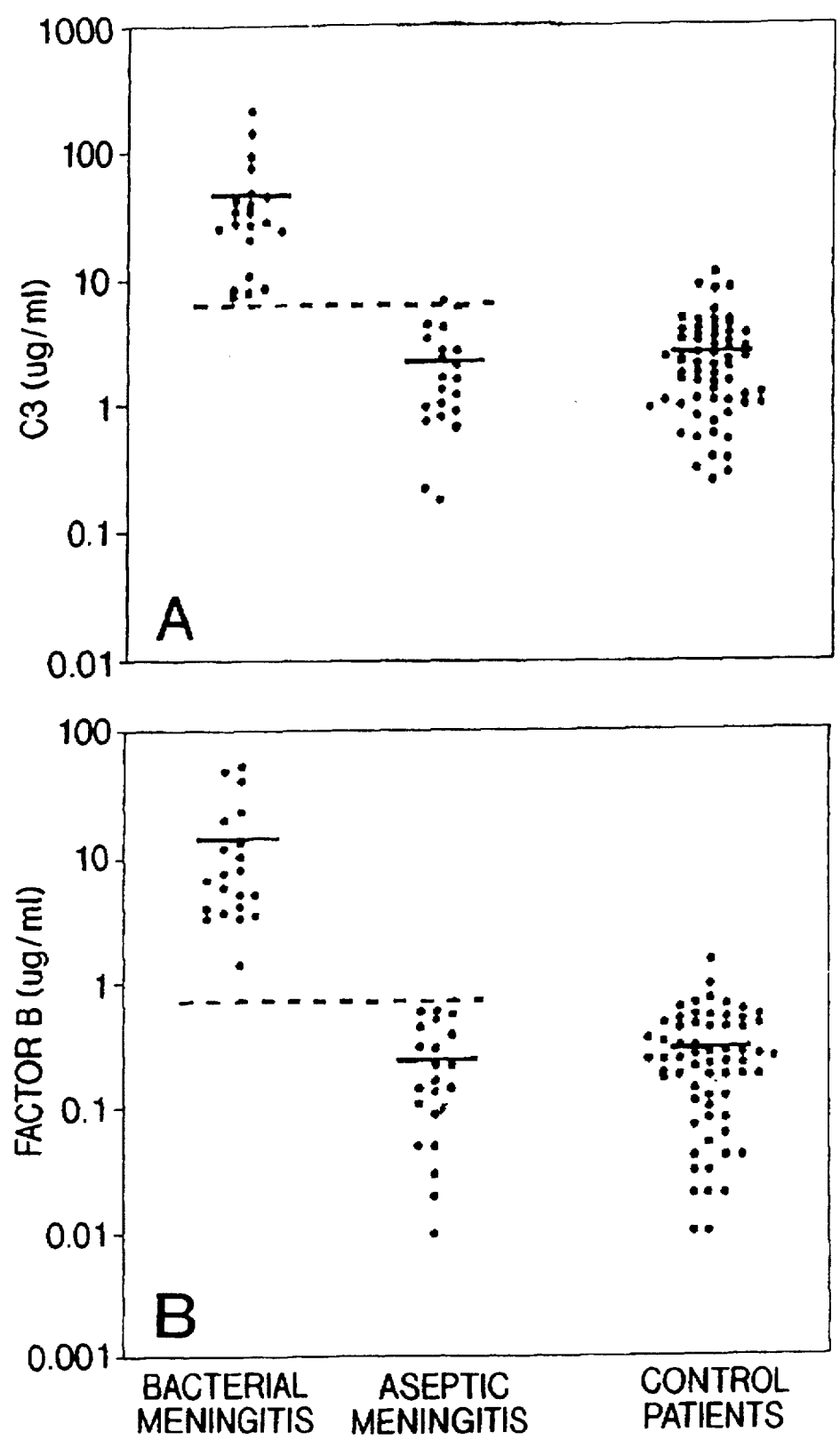
FIG. 1 shows the complement levels in the cerebrospinal fluid of patients with bacterial meningitis (BM; n=22), aseptic meningitis (BM; n=21), and controls (n=64). The quantitation of C3 (panel A) and factor B levels (panel B) was performed by enzyme-linked immunosorbent assy ELISA. Each point represents the mean of duplicate samples. The mean value for each group is shown by the horizontal bar. The dashed line indicates the cut-off level (mean of AM+2 SD) for differentiation between bacterial and aseptic meningitis.

The present invention is directed to a method for the differential diagnosis of bacterial meningitis in an individual in need of such diagnosis, comprising the steps of: measuring the levels of complement C3 and complement factor B in a sample from said individual; and determining whether said individual has bacterial meningitis based on the levels of complement C3 and complement factor B in the sample from said individual. Preferably, in this method of the present invention, the level of complement factor B indicative of bacterial meningitis is from about 0.65 µg/ml. Similarly, in the method of the present invention, the level of complement C3 indicative of bacterial meningitis is from about 5.8 µg/ml. Preferably, the sample is of cerebrospinal fluid.

The present invention is also directed to a method for the differential diagnosis of bacterial meningitis in an individual in need of such diagnosis, comprising the steps of: measuring the levels of complement factor B in a sample from said individual; and determining whether said individual has bacterial meningitis based on the levels of complement factor B in the sample from said individual. Preferably, in this method of the present invention, the level of complement factor B indicative of bacterial meningitis is from about 0.65 µg/ml. Preferably, the sample is of cerebrospinal fluid.

In another embodiment of the present invention, there is provided a method for the differential diagnosis of bacterial meningitis in an individual in need of such diagnosis, comprising the steps of: measuring the levels of complement C3 in a sample from said individual; and determining whether said individual has bacterial meningitis based on the levels of complement C3 in the sample from said individual. In the method of the present invention, the level of complement C3 indicative of bacterial meningitis is from about 5.8 µg/ml. Preferably, the sample is of cerebrospinal fluid.

The following examples are given for the purpose of illustrating various embodiments of the invention and are not meant to limit the present invention in any fashion.

EXAMPLE 1

Methods

Cerebrospinal fluid (CSF) levels of complement proteins C3 and factor B were assessed by specific ELISA in 22 patients with bacterial meningitis, 22 patients with aseptic meningitis, and 64 control patients.

EXAMPLE 2

Findings

C3 and factor B levels were significantly elevated in the cerebrospinal fluid of bacterial meningitis patients, compared to patients with aseptic meningitis or controls. For the diagnosis of bacterial meningitis, C3 and factor B cerebrospinal fluid levels showed a specificity of 90.5% and 100%, respectively, and a sensitivity and negative predictive value of 100% for both proteins. The positive predictive value for bacterial meningitis was 92% for C3 and 100% for factor B. The results of the present invention illustrate the determination of alternative pathway complement protein levels in the cerebrospinal fluid as a rapid and reliable diagnostic tool in the differential diagnosis of patients with acute infectious meningitis.

EXAMPLE 3

Patients and cerebrospinal fluid collection.

Cerebrospinal fluid samples were obtained by lumbar puncture from 42 patients with clinically suspected acute infectious meningitis on admission. Twenty-two patients were diagnosed with bacterial meningitis, based on positive bacterial culture or on detection of bacterial antigen in the cerebrospinal fluid. Diagnosis of *M. tuberculosis* meningitis was based on detection of acid-fast rods in the cerebrospinal fluid by Ziehl-Neelsen staining or on positive mycobacterial culture in Löwenstein medium. The pathogens were *S. pneumoniae* (n=13), *H. influenzae* (n=3), *N. menigitidis* (n=2), *L. monocytogenes* (n=1), *S. bovis* (n=1).

Patients with aseptic meningitis were diagnosed based on cerebrospinal fluid pleocytosis with a predominance of mononuclear cells, negative bacterial and fungal cerebrospinal fluid and blood cultures, negative results on cerebrospinal fluid antigen detection tests for *S. pneumoniae*, *H. influenzae*, and *N. menigitidis*, and full recovery without antibiotic treatment. No patient had received antibiotics or steroids prior to diagnostic lumbar puncture. After cerebrospinal fluid collection, the samples were centrifuged for 15 minutes at 1,500×g, and the supernatants were frozen at −20° C. until assayed. Control patients (n=64) comprised 20 patients with noninfectious neurological disease (intracranial vascular stenosis, polyneuropathy, cervical myelopathy, myoclonic syndrome, Arnold-Chiari malformation, and genuine epilepsy), 22 patients with lumbar puncture for diagnostic orthopedic intervention, and 22 patients who underwent diagnostic lumbar puncture, but were not diagnosed with a neurological disease. Cytological and biochemical analysis of the 64 cerebrospinal fluid samples from control patients was in the normal range.

EXAMPLE 4

Quantitation of complement levels

The cerebrospinal fluid levels of C3 and factor B were determined using specific enzyme-linked immunosorbent assays (ELISA), as previously described (Kossmann et al. 1997). The C3 ELISA used a goat anti-human-C3 antibody. The Factor B ELISA used a polyclonal rabbit anti-human Factor B antibody or a monoclonal goat-anti-human Factor B antibody. The assays are specific for human C3 and factor B, respectively, and are sensitive to 3 ng/ml. Before C3 and factor B concentrations were assessed, cerebrospinal fluid samples were thawed, and a "cocktail" of proteinase inhibitors containing Aprotinin (0.3 µM), Leupeptin (1 µM), Pepstatin (1 µM; Boehringer Mannheim) and EDTA (1 mM; Sigma) (all final concentrations) was added to each tube to prevent endogenous cleavage of complement proteins.

EXAMPLE 5

Statistical analysis

For the calculation of the operating characteristics of C3 and factor B cerebrospinal fluid levels in differentiating bacterial from aseptic meningitis, a cut-off level for each protein was defined at a mean value in aseptic meningitis+2 SD (López-Cortés et al. 1993, Glimaker et al. 1993). Using this criteria, the cut-off levels were set at 5.8 µg/ml for C3 and at 0.65 µg/ml for factor B. The operating characteristics were calculated as follows: sensitivity=rate of true positive tests in the bacterial meningitis population; specificity=rate of true negative tests in the aseptic meningitis population; negative predictive value=rate of patients with aseptic meningitis among the test-negative cases; positive predictive value=rate of patients with bacterial meningitis among the test-positive cases.

The statistical significance of differences between the mean complement levels in the cerebrospinal fluid of the different populations was calculated using the two-sample t-test assuming equal distribution, and confirmed by the non-parametric Wilcoxon rank sum test. P values of <0.05 were considered to be statistically significant. The correlation between complement cerebrospinal fluid levels and white blood cell count and protein levels in the corresponding cerebrospinal fluid samples was calculated using Pearson's correlation coefficient.

EXAMPLE 6

Results

FIG. 1 shows the levels of C3 (panel A) and factor B (panel B) in the cerebrospinal fluid of patients with infectious meningitis and controls. The mean C3 level in the cerebrospinal fluid of patients with bacterial meningitis was 44.35±47.91 µg/ml [mean ±SD] (range: 7.19–203.91 µg/ml), and significantly higher than in aseptic meningitis (2.16±1.82 µg/ml; range: 0.17–6.65 µg/ml. $P<0.003$) or in control patients (2.49±2.18 (g/ml; range: 0.1–10.84 (g/ml. $P<0.001$). Similarly, factor B cerebrospinal fluid levels were significantly elevated in bacterial meningitis (mean (SD: 13.0±15.14 µg/ml; range: 1.49–56.86 µg/ml) compared to aseptic meningitis (0.25±0.20 µg/ml; range: 0.01–0.61 µg/ml. $P<0.002$) or control patients (0.29±0.26 µg/ml; range: 0.01–1.5 µg/ml. $P<0.001$). For both proteins, the mean in the aseptic meningitis group was slightly lower than in the control group, but no significant differences were found.

In order to discriminate aseptic from bacterial meningitis according to the cerebrospinal fluid complement levels in the respective population, cut-off levels (mean value in aseptic meningitis +2 SD) were defined at 5.8 and 0.65 µg/ml for C3 and factor B, respectively. Detectable C3 and factor B levels above these limits in bacterial meningitis were 100% sensitive (21/21 patients). In aseptic meningitis, values above the cut-off level were observed in 2/21 (9.5%) patients for C3, and in none of the patients for factor B, thus resulting in specificities of 90.5% and 100% for C3 and factor B, respectively. The positive predictive value for bacterial meningitis was 92% for C3 and 100% for factor B, and both complement proteins had a 100% negative predictive value for bacterial meningitis.

Table I shows the demographic characteristics and initial cerebrospinal fluid laboratory analysis data of the 21 patients with bacterial meningitis. There was no correlation between cerebrospinal fluid complement levels and cerebrospinal fluid white blood cell count, cerebrospinal fluid protein concentrations, bacterial organism, or patients' outcome.

TABLE I

Demographic data and initial CSF findings of 21 patients with bacterial meningitis.

| Patient No. | Age/Gender | Pathogen | C3 CSF (µg/ml) | Factor B CSF (µg/ml) | CSF WBC (cells/µl) | % Poly | % Mono | CSF Protein (mg/dl) | CSF Glucose (mg/dl) | Outcome (GOS) |
|---|---|---|---|---|---|---|---|---|---|---|
| 1 | | S. pneumoniae | 91.03 | 52.8 | | | | | | |
| 2 | | S. pneumoniae | 26.14 | 5.41 | | | | | | |
| 3 | | S. pneumoniae | 33.77 | 6.21 | N/A | N/A | N/A | N/A | | |
| 4 | | S. pneumoniae | 40.09 | 12.69 | 3,000 | 90 | 10 | 197 | | |
| 5 | | S. pneumoniae | 27.11 | 7.15 | 427 | 89 | 7 | 157 | | |
| 6 | | S. pneumoniae | 20.15 | 3.71 | 140 | 56 | 44 | 104 | | |
| 7 | | S. pneumoniae | 8.31 | 4.26 | | | | | | |
| 8 | 14 years/m | S. pneumoniae | 46.44 | 56.86 | 26,070 | 96 | 4 | 1347 | <20 | 1 |
| 9 | 37 years/ | S. pneumoniae | 27.61 | 8.01 | 427 | 89 | 11 | 57 | 114 | 5 |
| 10 | 35 years/ | S. pneumoniae | 23.76 | 3.54 | 1,077 | 71 | 29 | 184 | 60 | 5 |
| 11 | 42 years/ | S. pneumoniae | 38.64 | 13.97 | 1,103 | 53 | 47 | 213 | 118 | 4 |
| 12 | 68 years/ | S. pneumoniae | 10.58 | 4.35 | 22 | 79 | 21 | 170 | 94 | 1 |
| 13 | 61 years/ | S. pneumoniae | 8.59 | 1.49 | 4,333 | 93 | 7 | 150 | 58 | 5 |
| 14 | 60 years/ | H. influenzae | 43.99 | 10.76 | 1,900 | N/A | N/A | 200 | N/A | 5 |
| 15 | | H. influenzae | 203.91 | 24.35 | | | | | | |
| 16 | | H. influenzae | 7.19 | 3.53 | | | | | | |
| 17 | 20 years/ | N. meningitidis | 71.91 | 21.21 | 3,371 | 97 | 3 | 600 | 20 | 6 |
| 18 | 16 years/m | N. meningitidis | 32.96 | 8.6 | 3,186 | 96 | 2 | 242 | 70 | 1 |
| 19 | 17 years/f | N. meningitidis | 136.43 | 42.79 | 15,700 | 100 | 0 | 579 | 0 | |
| 20 | 52 years/ | L. monocytogenes | 7.78 | 3.91 | 705 | N/A | N/A | 138 | 53 | 4 |
| 21 | 61 years/ | S. bovis | 24.9 | 5.38 | 9,300 | 95 | 5 | 382 | 30 | 5 | f = female; m = male; CSF = cerebrospinal fluid; WBC = white blood cell count; % Poly = percentage polynuclear cells;
% Mono = percentage mononuclear cells; GOS = Glasgow Outcome Scale score (Jennett and Bond 1975), assessed three months after discharge from the hospital;
1, death; 2, persistent vegetative state; 3, severe disability (conscious but disabled); 4, moderate disability (disabled but independent); 5, good recovery.

Complement has been discussed in the pathogenesis of bacterial meningitis by attracting blood-derived inflammatory cells into the subarachnoid space (Ernst et al. 1984, Tuomanen et al. 1986). The present invention demonstrates significantly elevated levels of complement components C3 and factor B in the cerebrospinal fluid of patients with acute bacterial meningitis. This finding agrees with an earlier report on elevated C3 levels and increased opsonic activity in the cerebrospinal fluid in bacterial meningitis (Zwahlen et al. 1982). However, Zwahlen and colleagues determined C3 levels by immunodiffusion, and did not express C3 levels as absolute concentrations, but only as percentage of activity in pooled serum (Zwahlen et al. 1982). Furthermore, the study by Zwahlen et al. suggested a correlation between high C3 cerebrospinal fluid levels and good recovery in a population of 27 patients with bacterial meningitis, a finding that could not be confirmed by the data presented here (see TABLE I).

In present invention, the C3 cerebrospinal fluid levels in bacterial meningitis were, on average, 20-fold higher than in patients with aseptic meningitis, while factor B cerebrospinal fluid levels were 57-fold higher, on average, in bacterial versus aseptic meningitis. The increases in bacterial meningitis are markedly higher than the elevated C3 and factor B levels previously reported in traumatic brain injury (Kossmann et al., 1997) and higher than in any other CNS disease (reviewed in Emmerling et al., 1997). In aseptic meningitis, C3 and factor B cerebrospinal fluid levels were similar to complement levels in the cerebrospinal fluid of control patients. More importantly, complement levels in the cerebrospinal fluid are of clinical value in distinguishing bacterial from aseptic meningitis. C3 and factor B cerebrospinal fluid levels were highly sensitive (both 100%) and highly specific (90.5% and 100%, respectively) for the diagnosis of bacterial meningitis, and associated with a negative predictive value of 100%, and a positive predictive value of 92% and 100%, respectively.

Although recent data from other studies suggest the determination of pro-inflammatory cytokines in the cerebrospinal fluid as markers for bacterial meningitis, such as tumor necrosis factor-α (TNF-αu), interleukin (IL$\beta$-1$\beta$), and IL-6 (Frei et al. 1990, Glimåker et al. 1993, López-Cortés et al. 1993, Dulkerian et al. 1995,), these mediators have shown either low sensitivity (TNF-α and IL-1$\beta$) (Frei et al. 1990, Glimåker et al. 1993, López-Cortés et al. 1993) or low specificity (IL-6) (Frei et al. 1990, Dulkerian et al. 1995) in discriminating aseptic from bacterial meningitis. The value of IL-8 cerebrospinal fluid levels in the differential diagnosis of infectious meningitis remains controversial (López-Cortés et al. 1995, Ostergaard et al. 1996, Sprenger et al. 1996).

The present invention demonstrates that the measurement of complement C3 in cerebrospinal fluid in the differential diagnosis of acute meningitis, can be used as a means to exclude bacterial infection (sensitivity and negative predictive value 100%), while complement factor B cerebrospinal fluid levels may be used for either exclusion or determination of bacterial meningitis (sensitivity, specificity, positive and negative predictive values 100%). The importance of determining complement cerebrospinal fluid levels for the diagnosis of bacterial meningitis is further illustrated by the example of patient 6 in this study, where routine analysis of the cerebrospinal fluid did not differentiate between aseptic and bacterial meningitis, whereas both C3 and factor B cerebrospinal fluid were indicative for bacterial infection, their levels being 3- to 4-fold higher than the cut-off value for bacterial meningitis (see TABLE 1).

Possible sources of elevated complement proteins in bacterial cerebrospinal fluid could be due to leakage from serum into the intrathecal compartment across a dysfunctional blood-brain barrier (BBB), since alterations of the BBB permeability represent a common feature of bacterial meningitis (Quagliarello & Scheld 1992), and normal C3 and factor B levels are several hundred-fold higher in serum than in cerebrospinal fluid (Kossmann et al. 1997). In addition, data demonstrate enhanced C3 and factor B mRNA expression by neurons and infiltrating myeloid cells in an experimental model of *Listeria monocytogenes* meningitis, suggesting intrathecal synthesis may contribute to elevated complement cerebrospinal fluid levels. In the present invention, the lack of correlation between total protein in the cerebrospinal fluid and complement cerebrospinal fluid levels further supports the hypothesis of intrathecal complement synthesis in patients with bacterial meningitis.

In conclusion, the determination of complement proteins, C3 and factor B in particular, in cerebrospinal fluid is a useful diagnostic tool in the differential diagnosis of meningitis. Rapid and accurate evaluation of patients with acute meningitis, by measuring C3 and factor B cerebrospinal fluid levels, will significantly reduce medical costs in terms of laboratory testing, hospital admissions and length of hospital stay.

The following references were cited herein:

Dulkerian S J, Kilpatrick L, Costarino A T, et al. Cytokine elevations in infants with bacterial and aseptic meningitis. *J Pediatr* 1995; 126: 872–6

Ernst J D, Hartiala K T, Goldstein I M, Sande A M. Complement (C5)-derived chemotactic activity accounts for accumulation of polymorphonuclear leukocytes in cerebrospinal fluid of rabbits with pneumococcal meningitis. *Infect Immun* 1984; 46: 81–6

Frei K, Nadal D, Fontana A. Intracerebral synthesis of tumor necrosis factor-a and interleukin-6 in infectious meningitis. *Ann New York Acad Sci* 1990; 594: 326–35

Glimåker M, Kragsbjerg P, Forsgren M, Olcén P. Tumor necrosis factor-a (TNFa) in cerebrospinal fluid from patients with meningitis of different etiologies: High levels of TNFa indicate bacterial meningitis. *J Infect Dis* 1993; 167: 882–9

Hoen B, Viel J F, Paquot C, Gérard A, Canton P. Multivariate approach to differential diagnosis of acute meningitis. *Eur J Clin Microbiol Infect Dis* 1995; 14: 267–74

Jennett B, Bond M. Assessment of outcome after severe brain damage. *Lancet* 1975; 1: 480–4

Kossmann T, Stahel P F, Morganti-Kossmann M C, Jones J L, Barnum S R Elevated levels of the complement components C3 and factor B in ventricular cerebrospinal fluid of patients with traumatic brain injury. *J Neuroimmunol* 1997; In press Lieu T A, Baskin M N, Schwartz J S, Fleisher G R. Clinical and cost-effectiveness of outpatient strategies for management of febrile infants. *Pediatrics* 1992; 89: 1135–44

Lindquist L, Linné T, Hansson L-O, Kalin M, Axelsson G. Value of cerebrospinal fluid analysis in the differential diagnosis of meningitis: A study in 710 patients with suspected central nervous system infection. *Eur J Clin Microbiol Infect Dis* 1988, 7: 374–80

López-Cortés L F, Cruz-Ruiz M, Gómez-Mateos J, Jiménez-Hernández D, Palomino J, Jiménez E. Measurement of levels of tumor necrosis factor-( and interleukin-1( in the cerebrospinal fluid of patients with meningitis of different etiologies: Utility in the differential diagnosis. *Clin Infect Dis* 1993; 16: 534–9

López-Cortés L F, Cruz-Ruiz M, G6mez-Mateos J, Viciana-Fernandez P, Martinez-Marcos F J, Pachón J. Interleukin-8 in cerebrospinal fluid from patients with meningitis of different etiologies: Its possible role as neutrophil chemotactic factor. *J Infect Dis* 1995; 172: 581–4

Ostergaard C, Benfield T L, Sellebjerg F, Kronborg G, Lohse N, Lundgren J. D. Interleukin-8 in cerebrospinal fluid from patients with septic and aseptic meningitis. *Eur J Clin Microbiol Infect Dis* 1996; 15: 166–9

Quagliarello V, Scheld W M. Bacterial meningitis: Pathogenesis, pathophysiology, and progress. *N Engl J Med* 1992; 327: 864–72

Rodewald L E, Woodin K. A., Szilagyi P G, Arvan D A, Raubertas R F, Powell K R. Relevance of common tests of cerebrospinal fluid in screening for bacterial meningitis. *J Pediatr* 1991; 119: 363–9

Spanos A, Harrell F E, Durack D T. Differential diagnosis of acute meningitis. An analysis of the predictive value of initial observations. *JAMA* 1989, 262: 2700–7

Sprenger H, Rösler A, Tonn P, Braune H J, Huffmann G, Gemsa D. Chemokines in the cerebrospinal fluid of patients with meningitis. *Clin Immunol Immunopathol* 1996; 2: 155–61

Tuomanen E, Hengstler B, Zak O, Tomasz A. The role of complement in inflammation during experimental pneumococcal meningitis. *Microb Pathog* 1986; 1: 15–32

Zwahlen A, Nydegger U E, Vaudaux P, Lambert P-H, Waldvogel F A. Complement-mediated opsonic activity in normal and infected human cerebrospinal fluid: Early response during bacterial meningitis. *J Infect Dis* 1982; 145: 635–46

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for the differential diagnosis of bacterial meningitis in an individual in need of such diagnosis, comprising the steps of:

measuring the levels of complement C3 and complement factor B in a cerebrospinal fluid sample from said individual; and determining whether said individual has bacterial meningitis by comparing the levels of complement C3 and complement factor B in the sample from said individual to the levels of complement C3 and complement factor B from a sample from an individual not suspected of having bacterial meningitis.

2. The method of claim 1, wherein said level of complement factor B indicative of bacterial meningitis is from about 0.65 µg/ml.

3. The method of claim 1, wherein said level of complement C3 indicative of bacterial meningitis is from about 5.8 µg/ml.

4. The method of claim 1, wherein said level of complement factor B is measured by enzyme-linked immunosorbent assay.

5. The method of claim 1, wherein said level of complement C3 is measured by enzyme-linked immunosorbent assay.

6. The method of claim 1, wherein said sample is cerebrospinal fluid.

7. A method for the differential diagnosis of bacterial meningitis in an individual in need of such diagnosis, comprising the steps of:

measuring the levels of complement factor B in a cerebrospinal fluid sample from said individual; and determining whether said individual has bacterial meningitis by comparing the levels of complement factor B in the sample from said individual to the levels of complement factor B from a sample from an individual not suspected of having bacterial meningitis.

8. The method of claim 7, wherein said level of complement factor B indicative of bacterial meningitis is from about 0.65 µg/ml.

9. The method of claim 7, wherein said level of complement factor B is measured by enzyme-linked immunosorbent assay.

10. The method of claim 7, wherein said sample is cerebrospinal fluid.

11. A method for the differential diagnosis of bacterial meningitis in an individual in need of such diagnosis, comprising the steps of:

measuring the levels of complement C3 in a cerebrospinal fluid sample from said individual; and determining whether said individual has bacterial meningitis by comparing the levels of complement C3 in the sample from said individual to the levels of complement C3 from a sample from an individual not suspected of having bacterial meningitis.

12. The method of claim 11, wherein said level of complement C3 indicative of bacterial meningitis is from about 5.8 µg/ml.

13. The method of claim 11, wherein said level of complement C3 is measured by enzyme-linked immunosorbent assay.

14. The method of claim 11, wherein said sample is cerebrospinal fluid.

* * * * *